United States Patent [19]

Sano et al.

[11] 4,230,555
[45] Oct. 28, 1980

[54] OXYGEN GAS ANALYZER USING A SOLID ELECTROLYTE

[75] Inventors: Seisuke Sano; Masato Maeda; Morimichi Iguchi, all of Musashio, Japan

[73] Assignees: Yokogawa Electric Works, Ltd.; Mitaka Instrument Co., Ltd, both of Tokyo, Japan

[21] Appl. No.: 73,915

[22] Filed: Sep. 10, 1979

[51] Int. Cl.³ ............................................. G01N 27/58
[52] U.S. Cl. ................................ 204/195 S; 427/225
[58] Field of Search ............ 204/195 S, 1 S; 60/276; 123/119 E, 119 EC; 422/98

[56] References Cited
U.S. PATENT DOCUMENTS

| | | | |
|---|---|---|---|
| 3,216,911 | 11/1965 | Kronenberg | 204/195 S X |
| 3,576,730 | 4/1971 | Spacil | 204/195 S |
| 4,080,276 | 3/1978 | Bode | 204/195 S |

*Primary Examiner*—G. L. Kaplan
*Attorney, Agent, or Firm*—Parmelee, Johnson, Bollinger & Bramblett

[57] ABSTRACT

An oxygen gas analyzer is provided having a solid-electrolyte partition wall generating a detection signal proportional to the difference between the oxygen concentrations on each side of the wall. Electrode films attached to each side of the wall are comprised of a metal powder having a particle size which becomes gradually smaller toward the partition wall. Platinum screens are bonded to the electrode films and leadwires are welded to the platinum screens for providing a detection signal therethrough. Advantageously, this structure provides improved bonding strength between the electrode films and the leadwires while also providing a short response time.

2 Claims, 7 Drawing Figures

OXYGEN GAS ANALYZER USING A SOLID ELECTROLYTE

BACKGROUND OF THE INVENTION

The present invention relates to an oxygen gas analyzer using a solid electrolyte.

FIG. 1 illustrates the general structure of an oxygen concentration cell (with zirconia or the like) constituting a sensor of an oxygen gas analyzer, in which 11 denotes a solid electrolyte forming a partition wall between two sides A and B. Electrode films 12a and 12b of platinum or the like are formed on the surfaces of the partition wall 11, and leadwires 14a and 14b are connected directly to the electrode films 12a and 12b, respectively. When a partial gas pressure introduces an unknown object gas to one side B of the oxygen concentration cell while a partial oxygen pressure introduces a standard gas to the other side A, then a voltage E expressed by the following equation is generated between the electrode films 12a and 12b:

$$E = Ti \frac{R \cdot T}{n \cdot F} \ln \frac{Px}{Ps}$$

in which
Ti: transport number of oxygen ions
R: gas constant
T: absolute temperature
n: number of electrons contributing to reaction
F: Faraday constant
Px: partial oxygen pressure representative of object gas to be analyzed
Ps: partial oxygen pressure representative of standard gas Therefore, the partial oxygen pressure representative of the object gas to be analyzed, that is, the concentration of the oxygen gas, can be obtained through measurement of the generated voltage E by the use of a voltmeter or the like via the leadwires 14a and 14b. In the known oxygen concentration cell of this type, it has been customary heretofore that the electrode films 12a and 12b are attached by baking to the partition wall 11. For this reason, rapid interconversion between the oxygen gas and the oxygen ions is rendered impossible thereby preventing the cell from attaining a short response time.

Moreover, according to the prior techniques, the leadwires 14a and 14b are connected either directly to the electrode films 12a and 12b or to platinum plates bonded to the electrode films, as shown in FIG. 1. The former method has a disadvantage of insufficiency in the mechanical strength against an external force or the like and may often cause an incomplete electrical connection. Although the latter method is capable of solving the problems observed in the former, it still fails in meeting the entire requirements thoroughly due to irregularity in the bonding strength.

SUMMARY OF THE INVENTION

It is an object of the present invention to provide an oxygen gas analyzer with a solid electrolyte capable of offering improved characteristics of short response time.

A further object of the invention is to provide a new and improved oxygen gas analyzer in which improved bonding strength of leadwires to the electrode films is provided without any irregularity.

In carrying out this invention in one illustrative embodiment thereof, an oxygen gas analyzer is provided having a solid-electrolyte partition wall with electrode films attached thereto, said partition wall generating a detection signal proportional to the difference between oxygen concentrations on each side of said partition wall. The electrode films are comprised of a metal powder having a particle size which becomes gradually smaller toward the partition wall. Platinum screens are bonded to the electrode films and leadwires are welded to the platinum screens for providing a detection signal therethrough.

BRIEF DESCRIPTION OF THE DRAWINGS

The invention, together with further objects, aspects and advantages thereof will be better understood from the following description taken in conjunction with the accompanying drawings.

DESCRIPTION OF THE PREFERRED EMBODIMENT

Figure 2:
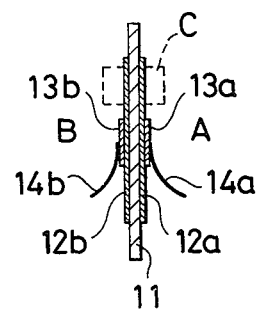
FIG. 2 is a sectional view of an oxygen concentration cell in accordance with the present invention.
Figure 4:
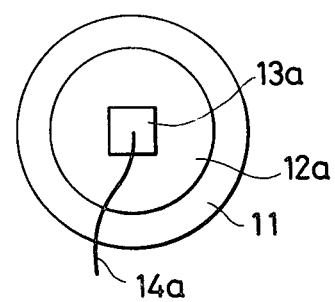
FIG. 4 is a right side view of FIG. 2.

Referring now to FIGS. 2 and 4, an oxygen concentration cell constituting a sensor of an oxygen gas analyzer according to this invention comprises a partition wall 11 of solid electrolyte such as zirconia; electrode films 12a and 12b of platinum or the like formed on the two sides of the partition wall 11; screens 13a and 13b composed of platinum and bonded to the electrode films 12a and 12b, respectively with a platinum paste; and leadwires 14a and 14b spot-welded to the platinum screens 13a and 13b. The platinum screen structure with the leadwires welded thereto is effective to reduce the irregularity in the bonding strength between the leadwires and the electrode films. In one experiment, 55-mesh screens of 0.3 mm-diameter platinum wire were cut to form 55 mm squares and then were bonded to electrode films 12a and 12b to produce platinum screens 13a and 13b, and further 0.3 mm-diameter platinum leadwires 14a and 14b were spot-welded thereto to constitute a concentration cell. In this structure, the bonding strength (or minimum load to cause separation) was in a range from 700 to 750 grams. In another experiment where 0.3 mm-diameter platinum leadwires 14a and 14b were conventionally bonded to the electrode films 12a and 12b, the bonding strength was in a range from 100 to 400 grams. Meanwhile, in the foregoing conventional example using 5 mm square plates of a 0.3 mm thickness, the strength range was between 300 to 1000 grams. As indicated by the aforesaid experimental data, it becomes possible in the above-described structure to attain a sufficiently high and stable bonding strength regardless of the skill and so forth of an operator or user. Moreover, the platinum screens employed in this invention are merely one third in cost as compared with platinum plates used heretofore, hence offering an ecomonic advantage as well.

It is to be understood that the shape of the platinum screens 13a and 13b is not particularly limited to a square shape alone, and that the diameter of the platinum wire need not be limited to 0.3 mm.

Figure 1:
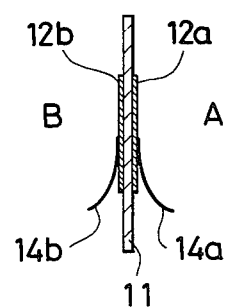
FIG. 1 shows the structure of a conventional oxygen concentration cell.
Figure 3:
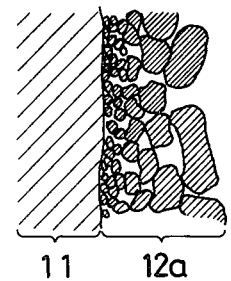
FIG. 3 is an enlarged view of a portion C in FIG. 2.
Figure 5:
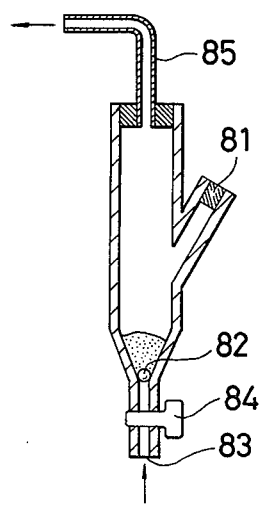
FIG. 5 illustrates the structure of a device designed for feeding a metal powder to a fusion spraying gun.

A detailed explanation will now be given on the structure of the electrode films 12a and 12b. As illustrated in the enlarged view of FIG. 3, the electrode film 12a embodied in this invention is so composed that the particle size of a metal powder thereof becomes gradually smaller toward the deepest region of the film which is that region closest to the partition wall 11. The optimal method for producing such electrode film is a process known as plasma fusion spraying. It is necessary, in this case, to gradually increase the particle size of the metal powder being fed to a fusion spraying gun. FIG. 5 shows an exemplary device designed for achieving this purpose, wherein an input port 81 is formed to introduce the metal powder into the device, and a ball 82 serves to prevent the metal powder from falling. A transport gas is supplied to a lower inlet 83 and, when a valve 84 is opened, the gas pushes up the ball 82 and passes via the inside of the device and a pipe to reach a fusion spraying gun (not shown). When a platinum powder is used, first the powder of a particle size range from several microns to several ten microns is introduced into the device through the input port 81, which is then closed with a plug, and subsequently the valve 84 is opened to widen its aperture by degrees. As a result, fine platinum particles of several or less microns are displaced upward and fed to the fusion spraying gun in the initial stage, and afterward the particle size of the platinum powder gradually increases up to several ten microns in the final stage to complete the supply.

Figure 6:
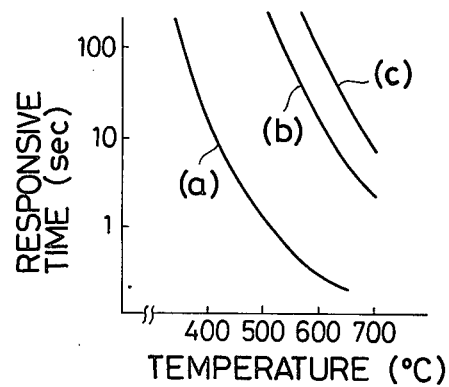
FIG. 6 graphically represents the response characteristics of the oxygen concentration cell embodied in this invention.

The response characteristic of the oxygen concentration cell of this invention is represented by a curve (a) in FIG. 6, in which the abscissa denotes the temperature of the oxygen concentration cell while the ordinate denotes the response time required until a 90-percent change appears in the output after the oxygen gas concentration is changed from 20 percent to 1 percent. The curves (b) and (c) in FIG. 6 represent the characteristics which are observed individually with respect to a baked platinum powder and a baked platinum paste on partition walls and are shown for comparison with the curve (a), wherein the partition walls employed are in the same shape and are composed of the same material (stabilized zirconia containing CaO 13 mol percent). As is obvious from FIG. 6, excellent response characteristics are attainable in the oxygen concentration cell of this invention.

Such outstanding response characteristics results principally from smooth diffusion of the gas in the oxygen concentration cell and also from the existence of many boundary areas where the partition wall, the meter powder and the space are in contact with one another.

Although the foregoing explanation covers the device manufactured by plasma fusion spraying, similar performance is also achievable by other methods as well. However, adoption of plasma fusion spraying eliminates the necessity of a binder or bonding agent and therefore provides a device with a less secular change.

Figure 7:
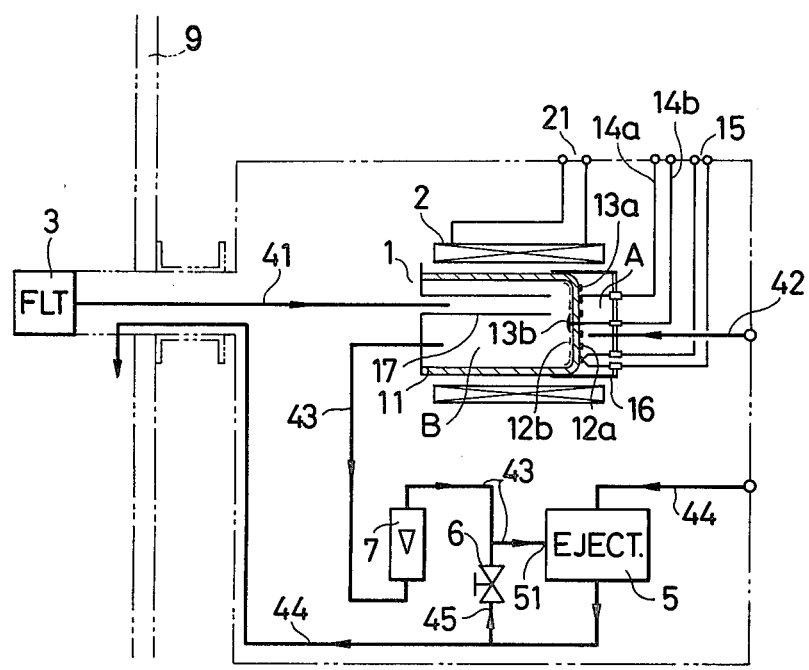
FIG. 7 illustrates the structure of a detector in the oxygen gas analyzer using a solid electrolyte.

FIG. 7 illustrates the structure of a detector in which the oxygen concentration cell of FIG. 2 functions as a sensor. The detector is secured directly to a wall 9 of a passage where an object gas to be analyzed flows, and generates a detection signal proportional to the oxygen concentration. (The detector is shaped into a probe whose fore end is insertable into the wall.) In FIG. 7, an oxygen concentration cell is in the shape of a test tube with a solid electrolyte member 11 and has electrode films 12a and 12b on the outside A and the inside B of its fore end, wherein platinum screens 13a and 13b are bonded to the electrode films and are equipped with leadwires 14a and 14b. A leadwire support 16 which is constituted by coupling a ring to the fore end of the oxygen concentration cell 1 and serves to hold the leadwires 14a, 14b and a thermocouple 15 in a fixed position relative to the concentration cell. This cell is maintained at a predetermined high temperature by a control system located in the periphery of the cell and consisting of a heater 2, the thermocouple 15 and a regulator (not shown). The control system is so disposed as to supply a standard gas to the side A via a passage 42 and also to continuously supply an object gas, which is to be analyzed, to the side B via a passage 41. The gas passage 41 connects a filter 3 with a chamber B in the oxygen concentration cell 1, and another gas passage 43 connects the chamber B with a suction inlet 51 of an ejector 5. The detector also includes a flow meter 7 in the gas passage 43; a gas circulation passage 45 for introducing the exhaust gas partially from the ejector 5 to the suction inlet 51; a flow-rate regulating valve 6 disposed in the gas circulation passage 45; and a gas passage 44 being coincident with the main passage of the ejector 5 and terminating in the vicinity of a point where the object gas to be analyzed is sampled.

When a gas flow occurs through the passage 44 in the detector, the object gas reaches the chamber B of the oxygen concentration cell 1 via the passage 41 and further advances to be sucked into the ejector 5 via the passage 43, and finally the gas is returned via the passage 44 to the vicinity of the sampling point. Thus, the gas is introduced directly into the chamber B of the oxygen concentration cell (not through diffusion). Consequently, there exists no time delay in sampling the object gas resulting in accelerating the response speed of the detector. Moreover, due to the provision of the gas circulation passage 45, the exhaust gas from the ejector 5 is permitted to flow partially into the suction inlet 51 of the ejector 5 via the passage 45 in accordance with the aperture of the valve 6. Therefore, the quantity of the object gas passing through the filter 3 is reduced by the amount flowing via the circulation passage. This signifies that clogging of the filter 3 is preventable over a long period of time by adjusting the aperture of the valve 6 to reduce the quantity of the object gas, which passes through the filter 3, to a proper value. Furthermore, if dust and so forth accumulate in the filter 3 and the gas passages 41, 43 and 44 with the lapse of the operation time increase the passage resistance, the aperture of the valve 6 may be adjusted to resume the initial flow rate of the object gas flowing into the chamber B of the oxygen concentration cell 1. Consequently, any measurement error resulting from flow rate variations can be prevented through proper adjustment of the valve aperture.

Thus, as described hereinabove, it becomes possible according to the present invention to implement an improved oxygen gas analyzer using a solid electrolyte with advantages of a short response time and a sufficiently high bonding strength of leadwires and so forth to the electrode films.

What is claimed is:

1. An oxygen gas analyzer having a solid-electrolyte partition wall with electrode films attached to the sides thereof and serving to generate a detection signal proportional to the difference between the oxygen concentrations on the two sides of said partition wall;

each of said electrode films comprising a metal powder having a particle size which gradually decreases toward the deepest region of the film adjacent said partition wall;

platinum screens bonded to said electrode films; and leadwires secured to said platinum screens for providing a detection signal therethrough.

2. The oxygen gas analyzer set forth in claim 1 wherein the gradually decreasing particle size of said metal powder is deposited on said partition wall by plasma fusion spraying.

* * * * *